(12) United States Patent
Anderson et al.

(10) Patent No.: US 6,306,818 B1
(45) Date of Patent: Oct. 23, 2001

(54) FRAGRANCE PRECURSORS

(75) Inventors: Denise Anderson, Zürich; Georg Frater, Winterthur, both of (CH)

(73) Assignee: Givaudan Roure (International) SA, Geneva (CH)

( * ) Notice: Subject to any disclaimer, the term of this patent is extended or adjusted under 35 U.S.C. 154(b) by 0 days.

(21) Appl. No.: 09/317,399

(22) Filed: May 24, 1999

Related U.S. Application Data

(63) Continuation-in-part of application No. 08/878,923, filed on Jun. 19, 1997, now abandoned.

(30) Foreign Application Priority Data

Jun. 24, 1996 (EP) .................................................. 96110157
Apr. 30, 1997 (EP) .................................................. 97107133

(51) Int. Cl.$^7$ ........................................................ A61K 7/46
(52) U.S. Cl. .................................. 512/2; 512/8; 512/11; 512/21; 512/25; 512/26; 512/27; 512/7; 424/65; 424/76.4; 510/101; 510/102; 510/105; 510/107; 558/260
(58) Field of Search ......................... 512/27, 26, 25, 512/21, 11, 8, 7, 2; 424/76.4, 65; 510/101, 102, 105, 107; 558/260

(56) References Cited

U.S. PATENT DOCUMENTS

| | | |
|---|---|---|
| 3,657,310 | 4/1972 | Frevel . |
| 4,033,993 * | 7/1977 | Bruns et al. .......................... 558/260 |
| 4,080,309 * | 3/1978 | Bruns et al. .............................. 512/8 |
| 4,395,370 | 7/1983 | Boden et al. . |
| 4,420,472 | 12/1983 | Boden et al. . |
| 5,098,886 * | 3/1992 | Narula et al. .......................... 512/22 |

FOREIGN PATENT DOCUMENTS

| | | |
|---|---|---|
| 2 302 732 | 3/1976 | (FR) . |
| 5186453 | 7/1993 | (JP) . |

OTHER PUBLICATIONS

World Patents Index; Japanese publication no. JP 5186453 (1993)(Derwent Accession No. 1993–269797)(English Abstract of documents B2).
Takeda, K., et al., *Synthesis*, 1987, 557–560.
Inanaga, J., et al. *Chemistry Letters*, 1993, 2:241–244.
Challis, A.A.L., et al., *J. Chemical Society*, 1947, 1692–1697.
Blaya, S., et al., *Tetrahedron*, 1995, 51(12):3617–3626.
Houlihan, F., et al., *Canadian J. Chemistry*, 1985, 63:153–162.
Schving, P., et al., *Bulletin de la Societe Chimique de France*, 1928, v. XLIII:857–859.
Vernaleken, H., *Ullmans Encyklopadic der technischen Chemie*, 1997, 591–593.
Derwent Abstract of FR 2 302 732 (document B1).

\* cited by examiner

*Primary Examiner*—Jill Warden
*Assistant Examiner*—Monique T. Cole
(74) *Attorney, Agent, or Firm*—Bryan Cave, LLP

(57) ABSTRACT

The invention relates to fragrance precursors, In particular, the invention relates to the use of several classes of compounds which may act as fragrance precursors, e,g., in cosmetic products such as deodorants and antiperspirants and in laundry products such as detergents and fabric softeners. These compounds are odorless, but upon contacting the skin as example, in skin care compositions or in personal care compositions, produce fragrances. The compounds also produce fragrances when used in the presence of lipases, e.g. as used in (laundry) detergents, thus providing a prolongation of the fabric scenting effect. The compounds under consideration are compounds of the formula I:

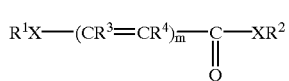

The substituents are defined in the specification.

12 Claims, No Drawings

FRAGRANCE PRECURSORS

CROSS-REFERENCE TO RELATED APPLICATION

The present application is a continuation-in-part of U.S. Ser. No. 08/878,923 filed on Jun. 19, 1997, now abandoned, the entire contents of which is hereby incorporated by reference.

FIELD OF THE INVENTION

The invention relates to fragrance precursors. In particular, the invention relates to the use of several classes of compounds which may act as fragrance precursors e.g. in cosmetic products such as deodorants and antiperspirants and in laundry products such as detergents and fabric softeners. These compounds are odorless, but upon contacting the skin as for example, in skin care compositions or in personal care compositions, produce fragrances. The compounds also produce fragrances when used in the presence of lipases, e.g. as used in (laundry) detergents, thus providing a prolongation of the fabric scenting effect.

BACKGROUND OF THE INVENTION

A principal strategy currently employed in imparting odors to consumer products is the admixing of the fragrance directly into the product. There are, however, several drawbacks to this strategy. The fragrance material may be too volatile, resulting in fragrance loss during manufacturing, storage, and use. Many fragrance materials are also unstable over time. This again results in loss during storage.

In some cases, fragrances are micro-encapsulated or treated with cyclodextrins to form inclusion complexes to help decrease volatility and improve stability. However, these methods are for a number of reasons often not successful. In addition, cyclodextrins may be too expensive for commercial processes.

In many consumer products, it is desirable for the fragrance to be released slowly over time. Microencapsulation and cyclodextrins have been used to provide slow-release properties, however, they are subject to the same limitations as above.

The present invention provides a solution for these and other problems.

SUMMARY OF THE INVENTION

The present invention provides compounds which are odorless, prior to application to the skin, but which release odorant molecules after application to the skin (that is, they provide a delayed release of the fragrance), in particular to the skin in the axilla. The compounds of the present invention also release odorant molecules when used in the presence of lipase-containing products, and, in this way, provide a prolongation of, e.g., the fabric scenting effect in detergents, fabric softeners, fabric softener sheets, and the like.

DETAILED DESCRIPTION OF THE INVENTION

In one embodiment of the present invention, a fragrance precursor of the formula I is provided:

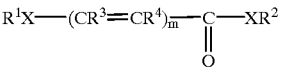

I wherein
  X is O or S;
  m is 0, 1 or 2, and n is 1–20;
  $R^1$ is the radical of an alcohol $R^1OH$ or a mercaptan $R^1SH$ having more than five carbon atoms;
  $R^2$ is the radical of an alcohol $R^2OH$ or a mercaptan $R^2SH$ having more than five carbon atoms; or
  $R^2$ is a substituted or unsubstituted $C_{1-40}$-alkyl or $C_{2-40}$-alkenyl radical, a carbocyclic radical or an aromatic radical, wherein this $R^2$ may in addition contain one or more hetero atoms, $—COOR^5$, and groups

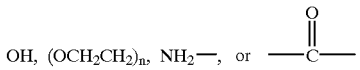

which groups may further be substituted by $—COOR^5$, wherein $R^5$ is the radical of an alcohol $R^5OH$ or a mercaptan $R^5SH$ having more than five carbon atoms, or
  $R^2$ is a polyalcohol radical or a sugar radical, of which one or more of the hydroxyl functions may be substituted as carbonates containing $R^1$ and/or $R^2$;
  wherein at least one of $R^1OH$, $R^1SH$, $R^2OH$, $R^2SH$, $R^5OH$ and $R^5SH$ has fragrance properties;
  $R^3$ and $R^4$ are H or $C_{1-6}$alkyl or
  $R^3$ and $R^4$ form a carbocyclic or heterocyclic ring.

In another embodiment of the present invention there is provided a compound of formula

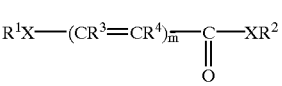

I wherein
  X is O or S;
  m is 0, 1 or 2, and n is 1–20;
  $R^1$ is the radical of an alcohol $R^1OH$ or a mercaptan $R^1SH$ having more than five carbon atoms;
  $R^2$ is the radical of an alcohol $R^2OH$ or a mercaptan $R^2SH$ having more than five carbon atoms; or
  $R^2$ is a substituted or unsubstituted $C_{1-40}$-alkyl or $C_{2-40}$-alkenyl radical, a carbocyclic radical or an aromatic radical, wherein this $R^2$ may in addition contain one or more hetero atoms, $—COOR^5$, and groups

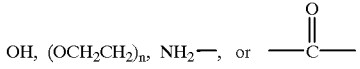

which groups may further be substituted by $—COOR^5$, wherein $R^5$ is the radical of an alcohol $R^5OH$ or a mercaptan $R^5SH$ having more than five carbon atoms, or
  $R^2$ is a polyalcohol radical or a sugar radical, of which one or more of the hydroxyl functions may be substituted as carbonates containing $R^1$ and/or $R^2$;
  wherein at least one of $R^1OH$, $R^1SH$, $R^2OH$, $R^2SH$, $R^5OH$ and $R^5SH$ has fragrance properties;

$R^3$ and $R^4$ are H or $C_{1-6}$alkyl or $R^3$ and $R^4$ form a carbocyclic or heterocyclic ring.

Another embodiment of the present invention is process for prolonging the effect of diffusion of the characteristic odor of an odoriferous alcohol or mercaptan as defined above which includes applying to the skin a fragrance precursor as defined above.

Another embodiment of the invention is a method of suppressing human body malodor by means of the fragrance precursors set forth above. This process includes applying to human skin a composition set forth above in a cosmetically acceptable carrier.

Examples of alcohols $R^1OH$ or $R^2OH$ are primary or secondary alcohols or phenols, such as for example:

hexyl alcohol*
2-hexyl alcohol*
heptyl alcohol*
octyl alcohol*
nonyl alcohol*
decyl alcohol*
undecyl alcohol*
lauryl alcohol*
myristic alcohol
3-methyl-1-pentanol
cis-3-hexenol*
cis-4-hexenol*
3,5,5-trimethyl hexanol
3,4,5,6,6-pentamethylheptan-2-ol (KOHINOOL, International Flavors & Fragrances)*
citronellol*
geraniol*
oct-1-en-3-ol
2,5,7-trimethyl octan-3-ol (CORPS ABRICOT, Givaudan-Roure)
2-cis-3,7-dimethyl-2,6-octadien-1-ol
6-ethyl-3-methyl-5-octen-1-ol (MEO PARF, Givaudan-Roure)*
3,7-dimethyl-oct-3,6-dienol*
3,7-dimethyloctanol (PELARGOL, Givaudan-Roure)*
7-methoxy-3,7-dimethyl-octan-2-ol (OSYROL, BBA)*
cis-6-nonenol*
5-ethyl-2-nonanol
6,8-dimethyl-2-nonanol (NONADYL, Givaudan-Roure)*
2,2,8-trimethyl-7 (8)-nonene-3-ol (CORPS LAVANDE, Givaudan-Roure)
nona-2,6-dien-1-ol
4-methyl-3-decen-5-ol (UNDECAVERTOL, Givaudan-Roure)*
dec-9-en-1-ol
benzylalcohol
2-methyl undecanol
10-undecen-1-ol
1-phenyl ethanol*
2-phenyl ethanol*
2-methyl-3-phenyl-3-propenol
2-phenyl propanol*
3-phenyl propanol*
4-phenyl-2-butanol
2-methyl-5-phenyl pentanol (ROSAPHEN, H+R)*
2-methyl-4-phenyl-pentanol (PAMPLEFLEUR, International Flavors & Fragrances)*
3-methyl-5-phenyl-pentanol (PHENOXANOL, International Flavors & Fragrances)*
2-(2-methylphenyl)-ethanol*
4-(1-methylethyl)benzene methanol
4-(4-hydroxyphenyl)butan-2-one*
2-phenoxy ethanol*
4-(1-methylethyl)-2-hydroxy-1-methyl benzene
2-methoxy-4-methyl phenol
4-methyl phenol
anisic alcohol*
p-tolyl alcohol*
cinnamic alcohol*
vanillin*
ethyl vanillin*
eugenol*
isoeugenol*
thymol
anethol*
decahydro 2-naphthalenol
borneol*
cedrenol (Givaudan-Roure)*
farnesol*
fenchyl alcohol*
menthol*
3,7,11-trimethyl-2,6,10-dodecatrien-1-ol
alpha ionol*
tetrahydro ionol*
2-(1,1-dimethylethyl)cyclohexanol*
3-(1,1-dimethylethyl)cyclohexanol*
4-(1,1-dimethylethyl)cyclohexanol*
4-isopropyl cyclohexanol (FOLROSIA® Givaudan-Roure)
6,6-dimethyl-bicyclo [3.3.1]hept-2-ene-2-ethanol (DIEPTOL, Dragoco)
6,6-dimethyl-bicyclo [3.1.1]hept-2-ene-methanol (MYRTENOL, BBA)*
p-menth-8-en-3-ol (ISOPULEGOL, Givaudan-Roure)*
3,3,5-trimethyl cyclohexanol
2,4,6-trimethyl-3-cyclohexenyl-methanol*
4-(1-methylethyl)cyclohexyl-methanol (MAYOL, Firmenich)*
4-(1,1-dimethylethyl)cyclohexanol
2-(1,1-dimethylethyl)-cyclohexanol (VERDOL, International Flavors & Fragrances)
2,2,6-trimethyl-alpha-propyl cyclohexane propanol (TIMBEROL, Dragoco)*
5-(2,2,3-trimethyl-3-cyclopentenyl)-3-methyl pentan-2-ol (SANDALORE® Givaudan-Roure)*
3-methyl-5-(2,2,3-trimethyl cyclopentyl-3-enyl)pent-4en-2-ol(EBANOL, Givaudan-Roure)*
2-ethyl-4(2,2,3-trimethyl cyclopentyl-3-enyl)but-2-en-1-ol (RADJANOL, Givaudan-Roure)*
4-(5,5,6-trimethylbicyclo[2.2.1]hept-2-yl)-cyclohexanol (SANDELA, Givaudan-Roure)*
2-(2-methylpropyl)-4-hydroxy-4-methyl-tetrahydropyran* (FLOROSA Q, Quest)*
2-cyclohexyl propanol*
2-(1,1-dimethylethyl)-4-methyl cyclohexanol (ROOTANOL, BASF)*
1-(2-tert-butyl-cyclohexyloxy)-2-butanol (AMBER CORE, Kao)*
1-(4-isoporpyl-cyclohexyl)-ethanol (MUGETANOL, H&R)*

Examples of thiols $R^1XH$ or $R^2XH$ are:
3-mercapto-1-hexanol
2-(1-mercapto-1-methylethyl)-5-methylcyclohexanone
methoxy-4-methyl-2-butane-2-thiol
thiogeraniol
thioterpineol.
*preferred alcohols It is a matter of course, that it is not possible to give a complete list of the odoriferous alcohols and mercaptans $R^1XH$ and $R^2XH$, which alcohols and mercaptans are liberated as a result of the desired cleavage of the carbonates of formula I by bacteria, in particular axilla bacteria, or lipases and which alcohols are then capable of imparting agreeable odors.

The skilled artisan is, however, quite aware of those alcohols and mercaptans, which provide a positive contribution to the fragrance compositions.

Examples of vinyl derivatives are derivatives of acrylic acid, etc.

The carbocycles encompass in particular, optionally substituted
cycloalkanes,
cycloalkenes,
polycycloalkanes, and
polycycloalkenes.

The aromatic rings encompass in particular, optionally substituted
one or more benzene rings, and
naphthalene.

The heterocycles encompass in particular, optionally substituted
pyridine,
pyrrole,
pyrrolidine,
pyrimidine,
furane,
thiophene,
dihydrofuran,
dihydropyran,
tetrahydrofuran,
tetrahydropyran,
quinoline,
furanose, and
pyranose.

Examples of polyalcohols are diols, e.g., diethylene glycol, propylene glycol, triethylene glycol, polyglycols; and triols, e.g. glycerol.

Examples of sugars are furanoside and pyranoside sugars, e.g. glucose and fructose.

The compounds of formula I may preferably be used as sustained release odorants but may also be used to mask or attenuate undesirable odors or to provide additional odors not initially present in consumer products, such as for example, cosmetic products destined for application to human skin. Non-limiting examples of such consumer products which are classified herein as "personal care products" include underarm deodorants or antiperspirants or other deodorants contacting the body, in hand lotions, baby powders, baby lotions, ointments, foot products, facial cleansers, body wipes, facial make-up, colognes, after-shave lotions, or shaving creams. Additional applications which may be classified herein as "home care products" include laundry detergents, fabric softeners, fabric softener sheets, automatic dishwasher detergents, and other lipase-containing consumer products.

Thus, as used herein, the phrase "consumer products" has its art recognized meaning. In the present invention, the phrase "consumer products" is intended to mean both "personal care products" and "home care products."

The compounds of formula I are odorless under normal temperature and atmospheric conditions (about 10–50 degrees Celsius and about 20 to 100% relative humidity). However, when applied to the body or when used in an application in the presence of lipases, they undergo a transformation in which the fragrant alcohol is released.

The compounds of formula I are not limited to any particular isomers. Thus, all possible stereo- and geometric isomers, as well as mixtures thereof are included within the scope of formula I.

The compounds of formula I, upon cleavage, provide alcohols having organoleptic properties and therefore permit the development of methods useful in enhancing the odor of consumer products. These compounds may be used individually in an amount effective to enhance the characteristic odor of a material. More commonly, however, the compounds are mixed with other fragrance components in an amount sufficient to provide the desired odor characteristics.

The amount required to produce the desired, overall effect varies depending upon the particular compounds of formula I chosen, the product in which it will be used, and the particular effect desired.

For example, depending upon the selection and concentration of the specific compound chosen, when it is added either singly or as a mixture e.g. to a deodorant or laundry product composition, at levels ranging from about 0.1 to about 10% by weight, or most preferred about 0.25 to about 4% by weight, an odorant, i.e. an odoriferous alcohol in an "organoleptically effective amount" is released when the product is used. This newly formed odorant serves to enhance the odor of the fragrance.

The compounds of formula I may accordingly be used in the manufacture of odorant compositions used in the preparation of cosmetic and laundry products. Such products include, for example, deodorants, antiperspirants, laundry detergents, and fabric softeners. As is evident from the above compilation, a broad range of known odorants or odorant mixtures may be used. In the manufacture of such compositions, the known odorants or odorant mixtures set forth above may be used according to methods known to the perfumer, such as, for example, those methods found in W.A. Poucher, Perfumes, Cosmetics, Soaps, 2, 7th Edition, Chapman and Hall, London 1974.

The compounds of formula I may be prepared by using standard methods known to the skilled chemist. These standard methods may be found in the chemical literature. For example, carbonates may be synthesized by reaction of a carbonic acid equivalent, e.g., phosgene, or a chemical equivalent of phosgene, with one or more alcohols or mercaptans in the presence of a base. Alternatively, reaction of a chloroformate which is another such carbonic acid equivalent. and an alcohol or mercaptan $R^1XH$ or $R^2XH$, in the presence of base, also yields a carbonate. This reaction is the substitution of a chloroformate by $R^1X$ or $R^2X$; see Comprehensive Organic Chemistry, Vol. 2 D. Barton, W. D. Ollis, Ed. p. 1070.

The vinyl carbonates may be prepared by β-addition of mercaptans or alcohols to propiolic acid esters, preferentially catalyzed by tertiary amines, such as trimethylamine or triethylamine, etc.

The following examples are set forth to illustrate the synthesis of the compositions of the present invention. These examples are provided for purposes of illustration only and are not intended to be limiting in any sense.

EXAMPLE 1

Carbonic acid bis-(2-phenyl-ethyl)ester

To a solution of 10.72 g triphosgene in 80 ml dichloromethane, 26.51 g phenethyl alcohol was added. While cooling in an ice bath, 17.16 g pyridine was dropped in over 45 minutes. Then, the reaction was stirred at room temperature for 62 hours. The reaction was diluted with dichloromethane, washed with aqueous HCl and aqueous $NaHCO_3$. The organic phase was dried, filtered and evaporated to dryness. The resulting crystals were recrystallized from 60 ml hexanes and then a second time from hexane:m- ethyl t.-butyl ether (50 ml:50 ml) to yield 15.48 g of colorless crystals.

NMR (CDCl$_3$)δ7.34–7.18 (m,10H), 4.31 (t, J=7.18 Hz,4H), 3.00 (t, J=7.17 Hz,4H).

EXAMPLE 2

Carbonic acid 2,3-bis-hex-3-enloxycarbonyloxy-propyl ester hex-3-enyl ester

To a solution of 32.30 g triphosgene in 100 ml dichloromethane, 34.45 g cis-3-hexenol was dropped in over 10 minutes while cooling in an ice/salt-bath. Then, 26.46 g pyridine was dropped in over 1 h 45 min. After stirring the reaction for 21 hours at room temperature the mixture was diluted with 200 ml pentane, filtered and evaporated to dryness to yield 51.14 g of a yellow oil. The raw product was then dropped in an ice cooled solution of 4.8 g glycerine and 30 ml pyridine in 100 ml dichloromethane over 1 h 45 min. After stirring the reaction for 48 h at room temperature, it was diluted with 200 ml ether and washed with 2×200 ml HCl 2N. The water phase was extracted with ether, then the combined organic phases were washed with NaHCO$_3$ and brine, dried and evaporated to dryness. The residue was purified by distilling off starting material first and then silica gel chromatography to yield 19.5 g of an oil.

NMR (CDCl$_3$)δ5.60–5.25 (m,6H), 5.16–5.06 (m,1H), 4.47–4.23 (m,4H), 4.18–407 (m,6H), 2.48–2.37 (m,6H), 2.13–1.99 (m,6H), 0.97 (t, J=7.48 Hz, 9H).

EXAMPLE 3

Carbonic acid 2,3-bis-phenethyloxycarbonyloxy-propyl ester phenethyl ester

According to the procedure of Example 2, Carbonic acid 2,3-bis-phenethyloxycarbonyloxy-propyl ester phenethyl ester was prepared starting from phenethyl alcohol and glycerol.

NMR (CDCl$_3$)δ7.35–7.20 (m,15H), 5.13–5.03 (m,1H), 4.41–4.19 (m,10H), 2.97 (t, J=7.17 Hz,6H).

EXAMPLE 4

Carbonic acid benzyl ester phenethyl ester

To a mixture of 29.96 g phenethyl alcohol and 30 ml pyridine in 150 ml dichloromethane, 60.5 g benzylchloroformate was dropped in over 1 h 45 min while cooling in an ice-bath. After stirring over night at room temperature, the reaction was diluted with ether, washed with 2N HCl, NaHCO$_3$, and water. After extraction with ether, the combined organic layers were dried and evaporated to dryness. The residue was purified by silica gel chromatography to yield the product: 52.5 g of a colorless oil.

NMR (CDCl$_3$) d 7.37–7.16 (m,10OH), 5.13 (s,2H), 4.34 (t, J=7.17 Hz, 2H), 2.96 (t, J=7.17 Hz, 2H).

According to the procedure of Example 4, the compounds set forth in Examples 5–9 were prepared from the starting materials indicated below:

EXAMPLE 5

Carbonic acid benzyl ester hex-3-enyl ester

Starting Material: cis-3-hexenol and benzylchloroformate.

NMR (CDCl$_3$)δ7.41–7.29 (m,5H), 5.58–5.44 (m,2H), 5.15 (s, 2H), 4.13 (t, J=7.02, 2H), 2.47–2.36 (m,2H), 2.11–1.97 (m,2H), 0.95 (t, J=7.5 Hz,3H).

EXAMPLE 6

Carbonic acid benzyl ester dec-9-enyl ester

Starting Material: dec-9-en-1-ol and benzyl chloroformate.

EXAMPLE 7

Carbonic acid 4-Allyl-2-methoxy-phenyl ester benzyl ester

Starting Material: Eugenol and benzyl chloroformate.

NMR (CDCl$_3$) d 7.44–7.26 (m,5H), 7.04–6.70 (m,3H), 6.03–5.83 (m,1H), 5.24 (s,2H), 5.14–5.02 (m,2H), 3.75 (s,3H), 3.34 (d, J=6.71 Hz,2H).

EXAMPLE 8

Carbonic acid hex-3-enyl ester 2-(2-hex-3-enyloxy-carbonyloxy-ethoxy)-ethyl ester Starting Material: cis-3-hexenol and diethylene glycol-bis-chloroformate.

NMR (CDCl$_3$) d 5.59–5.25 (m,4H), 4.30–4.25 (m,4H), 4.12 (t, J=7.01 Hz,4H), 3.78–3.70 (m,4H), 2.47–2.37 (m,4H), 2.13–1.99 (m,4H), 0.97 t, J=7.63 Hz,6H).

EXAMPLE 9

Carbonic acid 3,7-dimethyl-oct-6-enyl ester 2-[2-(3,7-dimethyl-oct-6-enyloxycarbonyloxy)-ethoxy]-ethyl ester Starting Material: citronellol and diethylene glycol-bis-chloroformate.

NMR (CDC3)δ5.12–5.04 (m, 2H), 4.30–4.14 (m, 8H), 3.75–3.70 (m, 4H), 2.04–1.91 (m, 4H), 1.74–1.15 (m, 22H), 0.92 (d, J=6.5 Hz, 6H).

EXAMPLE 10

(E)-3-Phenylethyloxy-acrylic acid ethyl ester

The reaction was performed in standard glassware under an atmosphere of N$_2$. To 100 ml of diethylether were added 9.8 g (0.1 mol) of propiolic acid ethyl ester, 12.2 g (0.1 mol) phenylethanol and 10.1 g (0.1 mol) of N-methylmorpholine. This solution was kept without stirring at room temperature for 24 hours. The mixture was evaporated under vacuum and the residue purified by bulb to bulb distillation (bp: 70–75° C., 0.006 mbar) to yield 15.7 g (88%) of an oil.

NMR (CDCl$_3$)δ7.57 (d, 1H); 7.37–7.13 (m, 5H); 5.20 (d, 1H); 4.15 (q, 2H); 4.04(t, 2H); 3.00 (t, 2H); 1.26 (t,3H).

EXAMPLE 11

(E)-Hex-(Z)-3-enyloxy-acrylic acid ethyl ester

The reaction was performed in standard glassware under an atmosphere of N$_2$. To 100 ml of diethylether were added 9.8 g (0.1 mol) propiolic acid ethyl ester, 10.2 g (0.1 mol) (Z)-3-hexenol and 10.1 g (0.1 mol) N-methylmorpholine. This solution was kept without stirring at room temperature for 24 hours. The mixture was evaporated under vacuum and the residue purified by bulb to bulb distillation (bp: 60–65° C.; 0.006 mbar) to yield 17.5 g (88%) of an oil.

NMR (CDCl$_3$)δ7.59 (d, 1H); 5.65–5.45 (m, 1H); 5.41–5.24 (m, 1H); 5.10 (d, 1H); 4.17 (q, 2H); 3.83 (t, 2H); 2.46 (q, 2H); 2.06 (qui, 2H); 1.28 (t, 3H); 0.98 (t, 3H).

In the same way, 3-phenethyloxy-acrylic acid phenethyl ester was obtained from phenethyl alcohol and propiolic acid phenethyl ester.

EXAMPLE 12

(E)-3-(3,7-Dimethyl-oct-6-enyloxy)-acrylic acid ethyl ester

The reaction was performed in standard glassware under an atmosphere of $N_2$. To 100 ml of diethylether were added 8.0 g (0.82 mol) propiolic acid ethyl ester, 12.8 g (0.82 mol) 3,7-dimethyl-oct-6-en1-ol and 8.3 g (0.82 mol) N-methylmorpholine. This solution was kept without stirring at room temperature for 24 hours. The mixture was evaporated under vacuum and the residue purified by bulb to bulb distillation (bp: 70–75° C.; 0.006 mbar) to yield 19.4 g (76%) of an oil.

NMR $(CDCl_3)\delta 7.58$ (d, 1H); 5.20 (d, 1H); 5.14–4.98 (m, 1H); 4.16 (q, 2H), 3.89 (t, 2H); 2.10–1.00 (m, 7H), overlapped: 1.69 (s, 3H); 1.60 (s, 3H), 1.28 (t, 3H); 0.92 (d, 3H).

EXAMPLE 13

(E)-3-Dec-9-enyloxy-acrylic acid ethyl ester

The reaction was performed in standard glassware under an atmosphere of $N_2$. To 150 ml of diethylether were added 9.8 g (0.1 mol) propiolic acid ethyl ester, 15.6g (0.1 mol) dec-9-en-1-ol and 10.1 g (0.1 mol) N-methylmorpholine. This solution was kept without stirring at room temperature for 24 hours. The mixture was evaporated under vacuum and the residue purified by bulb to bulb distillation (bp: 85–90° C.; 0.006 mbar) to yield 23.2 g (916%) of an oil.

NMR $(CDCl_3)\delta 7.59$ (d, 1H); 5.92–5.70 (m, 1H); 5.18 (d, 1H); 5.06–4.87 (m, 2H); 4.16 (q, 2H); 3.83 (t, 2H); 2.12–1.96 (m, 2H); 1.80–1.58 (m. 2H); 1.50–1.16 (m. 13H).

EXAMPLE 14

The following sulfur compounds were prepared:

Thiocarbonic acid 0-ethyl ester S-[1-methyl-1-(4methyl-2-oxo-cyclohexyl)-ethyl]ester from thio-dihydrocarvon and chloro formic acid ethylester.

4-Propyl-[1,3]oxathian-2-one from 3-mercapto-hexanol-1 and phosgene.

Carbonic acid 3-ethoxycarbonylsulfanyl-hexyl ester ethyl ester from 3-mercapto-hexanol-1 and chloro formic acid ethyl ester.

Additionally, the compounds listed below were prepared:

| $R^1OH$ | Synthesis via Example x from: | Product |
| --- | --- | --- |
| cis-3-hexenol | x = 1 cis-3-hexenol; triphosgene | Carbonic acid dihex-3-enyl ester |
| citronellol | x = 1 citronellol; triphosgene | Carbonic acid bis-(3,7-dimethyl-oct-6-enyl)ester |
| Rosalva (dec-9-en-1-ol) | x = 1 dec-9-en-1-ol; triphosgene | Carbonic acid didec-9-enyl ester |
| phenylethyl alcohol | x = 4 phenylethyl alcohol; 4-tert-butyl-cyclohexyl chloroformate | Carbonic acid 4-tert-butyl-cyclohexyl ester phenethyl ester |
| geraniol | x = 4 geraniol; 4-tert-butyl-cyclohexyl chloroformate | Carbonic acid 4-tert-butyl-cyclohexyl ester 3,7-dimethyl-octa-2,6-dienyl ester |

| $R^1OH$ | Synthesis via Example x from: | Product |
| --- | --- | --- |
| geraniol | x = 8 geraniol; diethylene glycol-bis-chloroformate | Carbonic acid 3,7-dimethyl-octa-2,6-dienyl ester 2-[(3,7-dimethyl-octa-2,6-dienyloxy-carbonyloxy)ethoxy]-ethyl ester |
| phenylethyl alcohol | x = 4 phenylethyl alcohol; butyl chloroformate | Carbonic acid butyl ester phenethyl ester |
| cis-3-hexenol | x = 4 cis-3-hexenol; butyl chloroformate | Carbonic acid butyl ester hex-3-enyl ester |
| geraniol | x = 4 geraniol; butyl chloroformate | Carbonic acid butyl ester 3,7-dimethyl-oct-2,6-dienyl ester |
| benzyl alcohol | x = 4 1,6-hexanediol; benzyl chloroformate | Carbonic acid benzyl ester 6-benzyloxycarbonyloxy-hexyl ester |
| ethyl vanillin | x = 7 ethyl vanillin; benzyl-chloroformate | Carbonic acid benzyl ester 2-ethoxy-4-formylphenyl ester |

EXAMPLE 16

Test cloth was washed with a lipase-containing detergent to which one or more delayed release fragrances of the present invention had been added. Headspace analysis of the wet and dry laundry indicated the presence of the fragrant alcohols. The alcohol level was higher than when the test cloth was washed with a lipase-containing detergent to which one or more fragrant alcohols were added.

EXAMPLE 17

Test cloth was washed with a lipase-containing detergent. Then, a fabric softener, containing one or more delayed release fragrances of the present invention, was added to the rinse cycle. Headspace analysis of the wet and dry laundry indicated the presence of the fragrant alcohols. The alcohol level was higher than when the test cloth was washed with a lipase-containing detergent and then a fabric softener, containing one or more delayed fragrant alcohols, was added to the rinse cycle.

EXAMPLE 18

Axilla bacteria cultures containing 0.1% precursor according to formula I were incubated for 20 hours at 30° C. After filtration from the cells, the presence of the parent alcohol was in each case detected by headspace-GC techniques and/or the majority of an 18 member panel.

The same tests were carried out with inactivated cultures (85°/20 min). The odor of the parent alcohols could not be detected after incubation, excluding therefore a hydrolysis by the medium or the culture.

EXAMPLE 19

The following set forth examples for the use of the delayed release fragrances of the present invention in various products. The methods of forming the following compositions are well known to those skilled in the art. All formulations may contain additional ingredients known to those skilled in the art, e.g. colorants, opacifiers, buffers, antioxidants, vitamins, emulsifiers, UV absorbers, silicones and the like. All products may also be buffered to the desired pH. All values are % w/w.

| Deo-colognes | | | | |
|---|---|---|---|---|
| Delayed Release Fragrances | 0.5 | 1.5 | 2.5 | 6.0 |
| Fragrance | 0.5 | 1.5 | 2.5 | 6.0 |
| Triclosan (Ciba Geigy) | 1.0 | — | 0.75 | 1.0 |
| Alcohol to | 100 | 100 | 100 | 100 |
| Deo-Sticks: Antiperspirant | | | | |
| Ethylene Glycol Monostearate | 7.0 | | | |
| Shea butter | 3.0 | | | |
| Neobee 1053 (PVO International) | 12.0 | | | |
| Generol 122 (Henkel) | 5.0 | | | |
| Kesscowax B (Akzo) | 17.0 | | | |
| Dimethicone Dow Corning 345 | 35.0 | | | |
| Aluminum Sesquichlorhydrate | 20.0 | | | |
| Delayed Release Fragrances | 0.5 | | | |
| Fragrance | 0.5 | | | |
| Antiperspirant | | | | |
| Steary Alcohol | 17.0 | | | |
| Castor Wax | 3.0 | | | |
| Talc | 5.0 | | | |
| Aluminum Zirconium Tetrachlorhydrate | 20.0 | | | |
| Delayed Release Fragrances | 1.0 | | | |
| Fragrance | 1.0 | | | |
| Dimethicone Dow 245 | to 100.0 | | | |
| Clear Deodorant Stick | | | | |
| Witconol APM | 43.0 | | | |
| Propylene Glycol | 20.0 | | | |
| Alcohol 39C | 20.0 | | | |
| Demin water | 7.0 | | | |
| Monamid 150ADD | 5.0 | | | |
| Millithix 925 | 2.0 | | | |
| Ottasept Extra | 0.5 | | | |
| Delayed Release Fragrances | 0.75 | | | |
| Fragrance | 0.75 | | | |
| Deodorant Stick | | | | |
| Propylene Glycol | 69.0 | | | |
| Demin Water | 21.8 | | | |
| Triclosan | 0.2 | | | |
| Sodium Stearate | 8.0 | | | |
| Delayed Release Fragrances | 0.5 | | | |
| Fragrance | 0.5 | | | |
| Alcohol free Deodorant Stick | | | | |
| PPG-3 Myristyl Ether (Witconol APM) | 36.0 | | | |
| Propylene Glycol | 36.0 | | | |
| Demin Water | 19.0 | | | |
| Triclosan | 0.25 | | | |
| Sodium Stearate | 7.75 | | | |
| Delayed Release Fragrances | 0.5 | | | |
| Fragrance | 0.5 | | | |
| Antiperspirant Aerosol | | | | |
| Absolute Ethanol | 15.0 | | | |
| Zirconium Aluminum tetrachlorhydrate | 5.0 | | | |
| Bentone 38 | 1.5 | | | |
| Delayed Release Fragrances | 0.75 | | | |
| Fragrance | 0.75 | | | |
| S-31 Hydocarbon propellant | to 100.0 | | | |
| Antiperspirant Pump | | | | |
| Demin water | 57.5 | | | |
| Aluminum Sesquichlorhydrate | 20.0 | | | |
| Triton X-102 (Union Carbide) | 2.0 | | | |
| Dimethyl Isosorbide (ICI) | 20.0 | | | |
| Delayed Release Fragrances | 0.25 | | | |
| Fragrance | 0.25 | | | |
| Roll-On | | | | |
| Dimethicone DC 354 (Dow Corning) | 69.0 | | | |
| Bentone 38 | 10.0 | | | |

-continued

| | |
|---|---|
| Rezal 36 GP (Reheis Chem. Co.) | 20.0 |
| Delayed Release Fragrances | 0.5 |
| Fragrance | 0.5 |

In the above, the following components were used:

| | |
|---|---|
| Triclosan | 5-chloro-2-(2,4-dichlorophenoxy)phenol |
| Neobee 1053 | glycerol tricaprate/caprylate |
| Generol 122 | soya sterol |
| Kesscowax B | cetyl alcohol and glycol polymer |
| Witconol APM | polypropylene glycol-3 myristyl ether |
| Monamid 150 ADD | cocoamide diethanolamine |
| Millithix 925 | dibenzylidene sorbitol |
| Ottasept Extra | quaternium 18 hectorite |
| Bentone 38 | quaternium 18 hectorite |
| Triton X-102 | octoxynol-13 |
| Dimethicone DC 354 | mixture of fully methylated linear siloxane polymers end-blocked with trimethylsiloxy units |
| Rezal 36 GP | Aluminium zirconium tetrachlorohydrexglycine |

The invention being thus described, it will be obvious that the same may be varied in many ways. Such variations are not to be regarded as a departure from the spirit and scope of the invention and all such modifications are intended to be included within the scope of the following claims.

What is claimed is:

1. A fragrance precursor composition, comprising an organoleptically effective amount of at least one compound of the formula

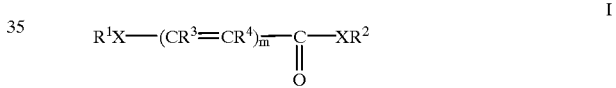

I wherein

X is O or S;

m is 0, 1 or 2, and n is 1–20;

$R^1$ is the radical of an alcohol $R^1OH$ or a mercaptan $R^1SH$ having more than five carbon atoms;

$R^2$ is the radical of an alcohol $R^2OH$ or a mercaptan $R^2SH$ having more than five carbon atoms; or if $R^2$ is a substituted or unsubstituted $C_{6-40}$-alkyl or $C_{6-40}$-alkenyl radical, a carbocyclic radical or an aromatic radical, then $R^2$ may in addition contain one or more hetero atoms, —$COOR^5$ and groups

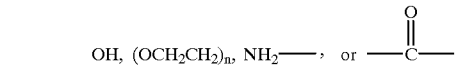

which groups may further be substituted by —$COOR^5$, wherein $R^5$ is the radical of an alcohol $R^5OH$ or a mercaptan $R^5SH$ having more than five carbon atoms, or $R^2$ is a polyalcohol radical or a sugar radical, of which one or more of the hydroxyl functions may be substituted as carbonates containing $R^1$ and/or $R^2$;

wherein at least one of $R^1OH$, $R^1SH$, $R^2OH$, $R^2SH$, $R^5OH$ and $R^5SH$ has fragrance properties;

$R^3$ and $R^4$ are H or $C_{1-6}$ alkyl or $R^3$ and $R^4$ form a carbocyclic or heterocyclic ring, with the exception of carbonic acid 4-allyl-2-methoxyphenyl ester benzyl ester, in a cosmetically acceptable carrier, wherein the, precursor is odorless.

2. The fragrance precursor of claim 1, wherein m is 0.

3. The fragrance precursor of claim 1 selected from the group consisting of Carbonic acid bis-(2-phenyl-ethyl)ester, Carbonic acid 2,3-bis-hex-3-enyloxycarbonyloxy-propyl ester hex-3-enyl ester, Carbonic acid 2,3-bis-phenethyloxycarbonyloxy-propyl ester phenethyl ester, Carbonic acid benzyl ester phenethyl ester, Carbonic acid benzyl ester hex-3-enyl ester, Carbonic acid benzyl ester dec-9-enyl ester, Carbonic acid hex-3-enyl ester 2-(2-hex-3-enyloxy-carbonyloxy-ethoxy)-ethyl ester, Carbonic acid 3,7-dimethyl-oct-6-enyl ester 2-[2-(3,7-dimethyl-oct-6-enyloxycarbonyloxy)-ethoxy]-ethyl ester, (E)-3-Phenylethyloxy-acrylic acid ethyl ester, (E)-Hex-(Z)-3-enyloxy-acrylic acid ethyl ester, (E)-3-(3,7-Dimethyl-oct-6-enyloxy)-acrylic acid ethyl ester, (E)-3-Dec-9-enyloxy-acrylic acid ethyl ester, Thiocarbonic acid 0-ethyl ester S-[1-methyl-1-(4-methyl-2-oxo-cyclohexyl)-ethyl]ester, 4-Propyl-[1,3]oxathian-2-one, and Carbonic acid 3-ethoxycarbonylsulfanyl-hexyl ester ethyl ester.

4. The fragrance precursor of claim 1 selected from the group consisting of Carbonic acid dihex-3-enyl ester, Carbonic acid bis-(3,7-dimethyl-oct-6-enyl)ester, Carbonic acid didec-9-enyl ester, Carbonic acid 4-tert-butyl-cyclohexyl ester phenethyl ester, Carbonic acid 4-tert-butyl-cyclohexyl ester 3,7-dimethyl-octa-2,6-dienyl ester, Carbonic acid 3,7-dimethyl-octa-2,6-dienyl ester 2-[(3,7-dimethyl-octa-2,6-dienyloxycarbonyloxy)ethoxy]-ethyl ester, Carbonic acid butyl ester phenethyl ester, Carbonic acid butyl ester hex-3-enyl ester, Carbonic acid butyl ester 3,7-dimethyl-oct-2,6-dienyl ester, Carbonic acid benzyl ester 6-benzyloxycarbonyloxy-hexyl ester, and Carbonic acid benzyl ester 2-ethoxy-4-formylphenyl ester.

5. A composition containing at least one of the fragrance precursors according to claim 1.

6. A composition containing at least one of the fragrance precursors according to claim 2.

7. A composition containing at least one of the fragrance precursors according to claim 3.

8. A composition containing at least one of the fragrance precursors according to claim 4.

9. A consumer product containing at least one of the fragrance precursors according to claim 1.

10. A consumer product according to claim 9 selected from the group consisting of underarm deodorants, antiperspirants, hand lotions, baby powders, baby lotions, ointments, foot products, facial cleansers, body wipes, facial make-up, colognes, after-shave lotions, shaving creams, laundry detergents, fabric softeners, fabric softener sheets, automatic and dishwasher detergents.

11. A process for prolonging the effect of diffusion of the characteristic odor of an odoriferous alcohol $R^1OH$ or $R^2OH$ or mercaptan $R^1SH$ or $R^2SH$, wherein $R^1$ and $R^2$ are as defined in claim 1, comprising applying to the skin a fragrance precursor as defined in claim 1.

12. A method of suppressing human body malodor which comprises applying to human skin a composition according to claim 5 in a cosmetically acceptable carrier.

* * * * *